(12) United States Patent
Contrada

(10) Patent No.: US 12,152,177 B2
(45) Date of Patent: Nov. 26, 2024

(54) MAGNETIC ADHESIVE FOR USE ON SKIN

(71) Applicant: Berry Global, Inc., Evansville, IN (US)

(72) Inventor: Svetlana Contrada, Manalapan, NJ (US)

(73) Assignee: Berry Global, Inc., Evansville, IN (US)

( * ) Notice: Subject to any disclaimer, the term of this patent is extended or adjusted under 35 U.S.C. 154(b) by 1101 days.

(21) Appl. No.: 16/454,659

(22) Filed: Jun. 27, 2019

(65) Prior Publication Data

US 2020/0002578 A1 Jan. 2, 2020

Related U.S. Application Data

(60) Provisional application No. 62/692,036, filed on Jun. 29, 2018.

(51) Int. Cl.
| | | |
|---|---|---|
| *C09J 7/38* | (2018.01) | |
| *C08K 3/22* | (2006.01) | |
| *C09J 121/00* | (2006.01) | |
| *C09J 133/06* | (2006.01) | |

(52) U.S. Cl.
CPC .............. *C09J 7/385* (2018.01); *C08K 3/22* (2013.01); *C09J 121/00* (2013.01); *C09J 133/06* (2013.01); *C08K 2003/2265* (2013.01); *C09J 2203/00* (2013.01)

(58) Field of Classification Search
CPC ........ C09J 7/385; C09J 121/00; C09J 133/06; C09J 2203/00; C09J 133/02; C09J 2301/408; C09J 2400/263; C09J 2421/00; C09J 2433/00; C09J 2463/00; C09J 2467/006; C09J 2475/00; C09J 2483/00; C09J 7/38; C08K 3/22; C08K 2003/2265; A61F 13/0253

See application file for complete search history.

(56) References Cited

U.S. PATENT DOCUMENTS

| | | | |
|---|---|---|---|
| 5,084,525 A | 1/1992 | Akutagawa et al. | |
| 5,151,318 A | 9/1992 | Strasilla et al. | |
| 5,547,599 A | 8/1996 | Wolfrey et al. | |
| 6,171,107 B1 * | 1/2001 | Milne | A61C 13/235 156/272.4 |
| 6,348,513 B1 | 2/2002 | Hilborn et al. | |
| 6,387,485 B1 * | 5/2002 | Bielek | C09J 7/38 428/209 |
| 6,506,494 B2 | 1/2003 | Brandys et al. | |
| 6,723,914 B1 * | 4/2004 | Kamei | H05K 9/0088 148/309 |
| 6,774,171 B2 | 8/2004 | Kassa | |
| 2002/0009582 A1 | 1/2002 | Golden | |
| 2003/0098436 A1 * | 5/2003 | Graham | H01F 41/16 427/547 |
| 2003/0152731 A1 * | 8/2003 | Deetz | B43L 1/008 428/40.1 |
| 2003/0155368 A1 * | 8/2003 | Giancarlo | B65H 35/0026 221/30 |
| 2003/0165652 A1 * | 9/2003 | Rivera | C09J 7/22 428/41.8 |

(Continued)

*Primary Examiner* — Kevin R Kruer
(74) *Attorney, Agent, or Firm* — Barnes & Thornburg LLP

(57) ABSTRACT

The present disclosure relates generally to an adhesive that can be used on organic tissue such as human skin, tapes including the adhesive with a magnetic filler such as a ferromagnetic filler, and methods of making the tapes.

16 Claims, 1 Drawing Sheet

(56) References Cited

U.S. PATENT DOCUMENTS

| | | | |
|---|---|---|---|
| 2005/0191337 A1* | 9/2005 | Gueret | A61Q 19/00 |
| | | | 424/448 |
| 2005/0274454 A1* | 12/2005 | Extrand | C09J 11/04 |
| | | | 428/323 |
| 2006/0172103 A1* | 8/2006 | Chang | C09J 7/22 |
| | | | 428/40.1 |
| 2008/0311405 A1 | 12/2008 | Wang et al. | |
| 2010/0294558 A1* | 11/2010 | Mitsui | H05K 9/0083 |
| | | | 174/377 |
| 2011/0014463 A1* | 1/2011 | Yaguchi | C09J 123/00 |
| | | | 252/62.55 |
| 2011/0020642 A1* | 1/2011 | Yaguchi | C09J 167/00 |
| | | | 252/62.51 R |
| 2012/0115382 A1 | 5/2012 | Contrada | |
| 2014/0023837 A1* | 1/2014 | Miller | G01L 1/12 |
| | | | 156/60 |
| 2016/0039154 A1* | 2/2016 | Mogi | B29C 33/16 |
| | | | 428/425.9 |
| 2016/0121018 A1* | 5/2016 | Watanabe | C09J 4/06 |
| | | | 523/118 |
| 2019/0261715 A1* | 8/2019 | Hunter | A61K 8/8152 |
| 2019/0289968 A1* | 9/2019 | Hunter | C09J 133/04 |
| 2020/0002578 A1* | 1/2020 | Contrada | C09J 7/385 |
| 2020/0281828 A1* | 9/2020 | Hunter | A61K 8/0241 |

* cited by examiner

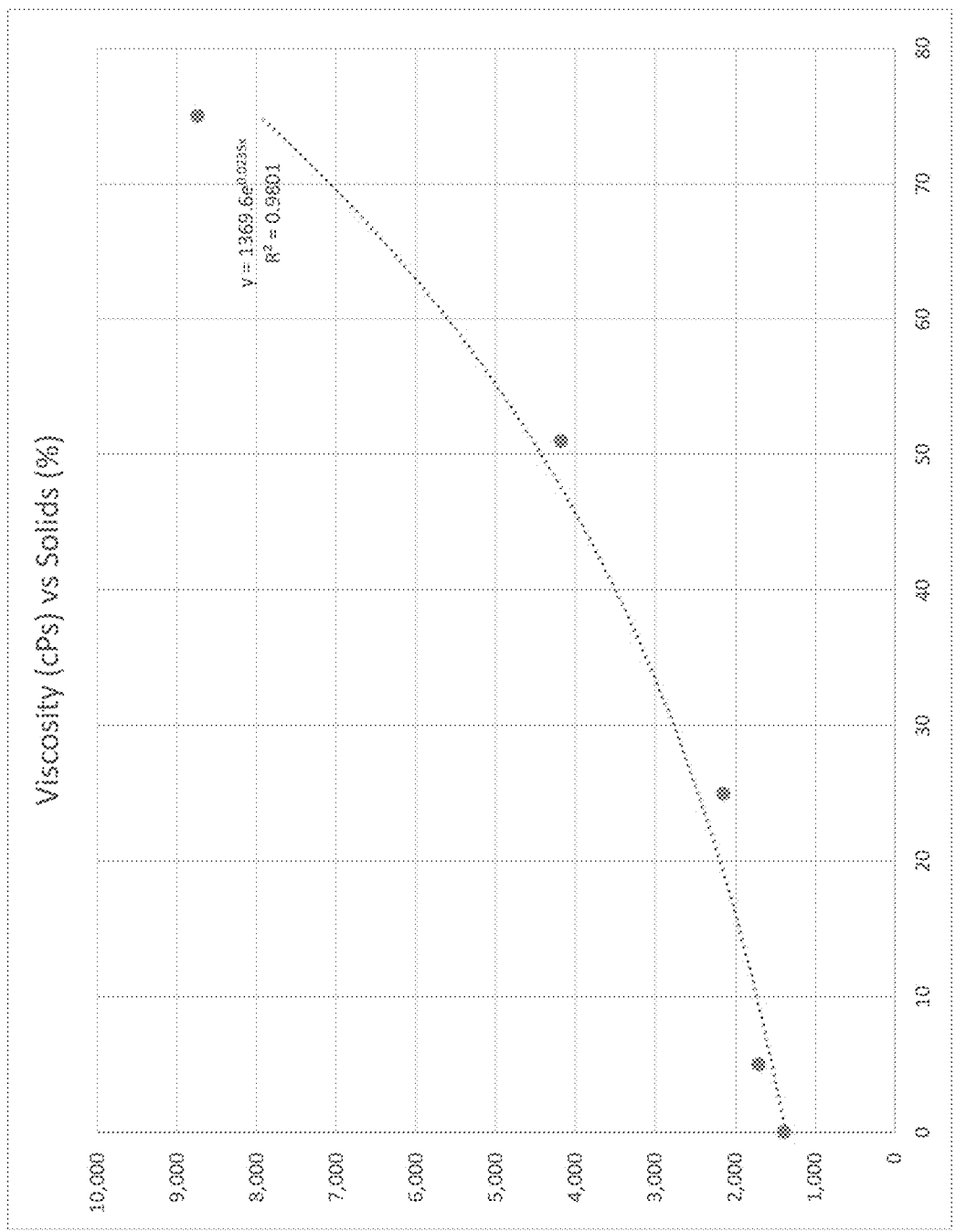

MAGNETIC ADHESIVE FOR USE ON SKIN

PRIORITY CLAIM

This application claims priority under 35 U.S.C. § 119(e) to U.S. Provisional Application Ser. No. 62/692,036, filed Jun. 29, 2018, which is expressly incorporated by reference herein.

TECHNICAL FIELD

The present disclosure relates generally to an adhesive with magnetic filler that can be used on organic tissue such as human skin.

BACKGROUND

The present disclosure relates to an adhesive. More particularly, the present disclosure relates to a bio-compatible adhesive that may include a magnetic component and that may be suitable for use on skin.

SUMMARY

According to the present disclosure, an adhesive may include a magnetic filler yet be bio-compatible. The adhesive may be suitable for skin contact for extended periods of time and/or suitable for medical applications, for example, medical applications facilitated by magnetic response and/or sensitivity of the material to an applied or external magnetic field. In some embodiments, an adhesive with a ferromagnetic filler may be usable as a component of a medical device, such as a sensor sensitive to changes in a magnetic field, and/or wearable devices facilitated by direct attachment and/or hold to skin. In some embodiments, an adhesive with a magnetic filler such as a ferromagnetic filler may be used in medical patches or the like for attachment to skin with extended skin wear time under active wear conditions, such as during exercise and/or under wet conditions often detrimental to the ability of a typical adhesive to adhere to skin such as while taking a shower or swimming.

In one aspect, for instance, some embodiments may provide an adhesive composition that includes a polymer matrix base pressure sensitive adhesive suitable for use on skin and a ferromagnetic filler. The polymer matrix base pressure sensitive adhesive may be present in amount of about 5-95% and the ferromagnetic filler may be present in an amount of about 5-95%.

In another aspect, for instance, some embodiments may provide a tape including a bio-compatible adhesive composition suitable for medical applications, for example. The adhesive composition may include a base pressure sensitive adhesive and a magnetic filler. The tape may include a substrate suitable for lamination with the bio-compatible adhesive. The adhesive composition may be laminated to the substrate to form a bio-compatible magnetic adhesive tape.

In yet another aspect, for instance, some embodiments may provide a method of providing a bio-compatible magnetic adhesive tape. A base adhesive and a magnetic filler may be provided. The based adhesive and magnetic filler may be combined into a magnetic adhesive composition. A substrate may be coated with the magnetic adhesive composition to provide the magnetic adhesive tape.

Additional features of the present disclosure will become apparent to those skilled in the art upon consideration of illustrative embodiments exemplifying the best mode of carrying out the disclosure as presently perceived.

BRIEF DESCRIPTION OF THE DRAWING

The detailed description particularly refers to the accompanying FIGURE in which:

FIG. 1 is a graph showing the relationship between viscosity and percent solids of some adhesive compositions presented herein.

DETAILED DESCRIPTION

Embodiments now will be described more fully hereinafter with reference to the accompanying FIGURE and Tables, in which some, but not all embodiments are shown. As used in the specification, and in the appended claims, the singular forms "a", "an", "the", include plural referents unless the context clearly dictates otherwise.

The terms "substantial" or "substantially" may encompass the whole as specified, according to certain embodiments, or largely but not the whole specified according to other embodiments.

Illustrative embodiments of this disclosure relate to compositions or composite materials having a polymer matrix that includes a magnetic filler such as a ferromagnetic filler. For example, a polymer matrix may include adhesives such as pressure sensitive adhesives that may include a ferromagnetic filler, as well as articles using the composite materials, compositions, polymer matrices, and/or adhesives. An adhesive or composition including a magnetic filler may be provided in a magnetized or in a non-magnetized condition. The magnetic filler and/or an adhesive or composition including the magnetic filler may or may not display magnetic properties and/or other properties associated with the magnetic filler. The adhesives may be bio-compatible or non-cytotoxic, for example as determined by passing a standardized test such as ISO 10993-5 (elution cytotoxicity test). Moreover, the adhesives or compositions may be functional when applied in a thickness of about 0.3 mil to about 7 mil or about 0.0076 mm to about 0.18 mm, for example when applied in a thickness of about 2 mil or about 0.05 mm. The adhesive or composition may be suitable for coating on a surface or substrate by conventional pressure sensitive adhesive (PSA) coating manufacturing techniques, such as techniques typically used with conventional solvent based PSAs, such as reverse roll, knife over roll, and/or by doctor blade, or any other method, or any combination thereof, for example to form a tape and/or coated substrate.

It is understood that other techniques could be used to mix a ferromagnetic filler with a base polymer matrix, such as hot melt adhesive extrusion and/or other application techniques, for example where a mixed polymer with a ferromagnetic filler forms a tape, in an unsupported adhesive form, between two or more layers of release liner, and/or in tape form with a magnetic adhesive coated on a substrate and covered with a protective liner. In some embodiments the coated magnetic composition in tape form does not require a release liner, as it may not have pressure sensitive properties, adhesion to some substrates such as steel or plastic, and/or probe tack, as discussed in further detail below. In some embodiments, the base polymer matrix for the magnetic PSA compositions may be selected from, but is not limited to, a group including conventional and/or commercially available rubber based, acrylic, polyurethane, and/or silicone, and/or mixtures thereof. It is understood that medical grade base adhesives and/or polymer matrices may be used, though it is possible that some base adhesives that are not medical grade or have not been proven medical grade could be used.

The adhesives or compositions could be provided with or without pressure sensitive properties, for example as tested or established by conventional PSA testing methods including adhesion, tack, and/or shear. For another example, the adhesive or composition could be provided without pressure sensitive properties when tested by these or other methods. For instance, the adhesive or composition may display test results indicating substantially zero adhesion, zero tack, and/or zero shear, while feeling tacky to the touch or having a tacky or sticky tactile property, and it may subjectively and/or objectively exhibit adhesion and/or hold or stick to skin for extended periods of time.

The unique property of holding to organic tissue such as human skin for extended periods of time, while displaying essentially no measurable adhesion to substrates such as steel and plastic, and essentially no probe tack, along with other properties, were among the unexpected results found when testing some embodiments of adhesive compositions having magnetic filler as described herein. For instance, it was found that adhesives or compositions, and/or articles coated with the adhesives or compositions, lost pressure sensitive properties including tack, adhesion, and hold as tested by conventional PSA methods, yet the adhesives still felt tacky to the touch and were able to adhere to skin well for long periods of time (e.g., 18 hours or more) without detaching, lifting, or falling off, even under active wear conditions. Examples of active wear conditions that were tested include running, using exercise equipment up to about an hour, and taking showers. Moreover, such adhesives did not exhibit irritation (e.g., redness of the skin) and were able to pass bio-compatibility tests such as ISO 10993-5 (elution cytotoxicity) indicating the adhesives were non-cytotoxic. Furthermore, the novel adhesive compositions received scores of zero (0) per ISO 10993-5, indicating no adverse effect on living cell cultures. The adhesive or compositions including magnetic filler were functional at unusually high filler contents (e.g., over about 50 wt. %) when compared to conventional adhesive compositions including inorganic filler such as talc or silica.

Illustrative embodiments may include an adhesive for use on skin, for example in medical applications or for applying medical devices to the skin. For example, some embodiments may include an adhesive or composition that includes an acrylic or rubber based PSA and/or a filler. A polyacrylate or an acrylic base adhesive may be provided and may be combined with a solvent such as an organic solvent, or it may be combined with a filler such as a magnetic filler, or both. In other embodiments, a rubber adhesive may be provided and may be combined with a solvent such as an organic solvent, or it may be combined with a filler such as a magnetic filler, or both. It is understood that, if included, a solvent may include a blend of solvents and/or other components. For example, a solvent blend may include any or all of heptane, toluene, ethyl acetate, isopropyl alcohol, and methyl ethyl ketone, in any of a variety of relative ratios or amounts.

A polyacrylate suitable for use in an illustrative embodiment includes a polymer in which the primary components are monomers of acrylic acid and acrylic or meth(acrylic) esters. Such polymers are also often referred to as acrylic adhesives. Commercial medical and/or transdermal grade polyacrylates are available from Henkel (e.g., DURO-TAK® 129A) or Ashland (e.g., Aroset® 280), or other manufactures of PSAs. In illustrative examples, the amount of polyacrylate in an adhesive in accordance with the present disclosure may be between about 5% and 95% by weight.

Another suitable base adhesive that may be used is a rubber base adhesive. Synthetic rubber based adhesives may include styrene-isoprene-styrene (SIS), styrene-butadiene-styrene (SBS), and/or polyisobutylene (PIB), and/or mixtures thereof, and may include tackifiers, such as terpene phenolic resins, rosin ester resins, and/or hydrocarbon resins, and/or mixtures thereof. One example of a commercial rubber adhesive is MORSTIK™ 153, available from The Dow Chemical Company.

Some embodiments including an acrylic or rubber adhesive, and/or a solvent or solvent blend, may also include a filler for any of a variety of reasons, including but not limited to providing or enhancing one or more particular properties. For example, a magnetic filler may be provided so that the composition may be magnetized or made magnetic. An example of a magnetic filler that may be used is a ferromagnetic filler. For instance, in some embodiments strontium ferrite, such as strontium hexaferrite with molecular formula $SrFe_{12}O_{19}$ may be used. It is understood that strontium hexaferrite, other forms of strontium ferrite, and/or other magnetic filler materials may be used with or without one or more surface treatments, and/or protective coatings, such as anticorrosion coatings. A commercially available strontium ferrite powder that may be used in illustrative embodiments of an adhesive composition is a low energy embedding powder, which may have any or all of the properties of: a pH level of about 10 to about 11; a melting point of about 1500° C.; a relative density of about 5 $g/cm^3$ and/or an average particle size in the range of about 1.65 microns to about 4.6 microns. A powder with any or all of these properties may be included to provide an adhesive composition with desirable properties, such as a smooth coating, for example. Such a strontium ferrite powder is commercially available, for example, from Hoosier Magnetics, Inc. Commercially available grades of strontium ferrite powder include HM 406, 410, 413, 418, 430, 443, 206, 243, and 239; Starmag 444; and Xmag 450. In illustrative embodiments and examples provided, which are discussed more below, HM410 with an average particle size of about 2.0 microns to about 2.5 microns was found to be a suitable grade of the ferromagnetic filler. HM410 was found to provide a smooth coating in the examples provided below.

One or more rheological additives may be used in adhesive formulations including magnetic filler to reduce and/or prevent sedimentation of the magnetic filler from the adhesive over time. Rheological additives may, for example, be clay based. Some examples of clay based rheological additives that may be used with magnetic filler in a formulation could include organic derivatives of a bentonite clay or a hectorite clay.

Unexpected results were found when using magnetic filler such as ferromagnetic filler and such as strontium ferrite. For instance, it was found that adhesives or compositions, and/or articles coated with the adhesives or compositions, lost pressure sensitive properties including tack, adhesion, and static shear as tested by conventional PSA methods, yet the adhesives still felt tacky to the touch and were able to adhere to skin well for long periods of time (e.g., 18 hours or more) without detaching, lifting, or falling off, even under active wear conditions. Moreover, such adhesives did not exhibit skin irritation (e.g., redness of the skin) and were able to pass bio-compatibility tests such as ISO 10993-5 (elution cytotoxicity) indicating the adhesives were non-cytotoxic.

The biocompatibility and elution cytotoxicity test results were unexpected. The ferromagnetic filler used, including strontium ferrite in powder form, is not currently used in the medical industry as a filler in PSAs intended for use in medical applications requiring skin contact. It was unexpected that the adhesive compositions generated using the magnetic filler would pass Elution Cytotoxicity ISO 10993-5. It was also unexpected that such adhesive compositions would pass such tests with a score of zero (0), indicating no adverse effect on living cells. Conventional medical PSAs need to achieve a score equal or below two (2) to pass this test. It was unexpected that there would be zero adhesion, zero static shear, and zero probe tack and yet the composition would hold to skin for extended periods of time through active wear conditions. Adhesion testing, probe tack testing, and bio-compatibility testing was conducted according to accepted standards discussed in further detail below.

The adhesive compositions, which may include a base adhesive, one or more solvents, and/or filler, may be applied to a substrate to provide a tape. Any of a variety of substrates may be used, such as, for example, a cloth substrate or a film substrate. It is understood that the adhesive compositions described herein may be used with virtually any substrate or any combination of substrates, with other backing materials or structures, with medical devices and/or sensors, with devices for use on skin, with any combination thereof, or without a substrate, backing, or other structure. In some illustrative embodiments, adhesive compositions were applied to a non-woven cloth substrate. Commercial grade non-woven cloth is available from, for example, SONTARA® (e.g., Style 8010). In other illustrative embodiments, adhesive compositions were applied to a plastic film substrate. Commercial grade 2 mil PET film, for example, is available from Transcendia (e.g., TransPET® GPHH-F). It is understood that other substrates may be used instead of or in addition to a non-woven cloth substrate and/or a plastic film substrate to which the composition may be applied. For example, other substrates may include any or all of foil, foamed substrates, laminated or multilayer substrates that may include film, foil, non-woven and/or foam substrates, other material, or any combination thereof.

Testing

Various embodiments were provided as described herein, including Examples 1 through 12 described in further detail below. These examples were tested in various ways according to the methods discussed below. Data and results from those tests are provided in Tables 1 through 9, FIG. 1, and discussed herein.

Percent Solids

As used herein, percent solids, and weight percent (or wt. %) solids may refer to the amount of non-volatile matter in a mixed sample expressed as a weight percent of the total sample composition weight. For the data presented herein, percent solids or weight percent solids was tested with an MX-50 Moisture Analyzer, using a 2 gram sample weight and a temperature setting of about 150° C. until the weight change did not exceed 0.0001 gram.

Viscosity Per ASTM D1084

Solution viscosity of wet adhesive samples was tested according to ASTM D1084-16 "Standard Test Method for Viscosity of Adhesives". A Brookfield synchroelectric viscometer was used to test viscosity, using a range of about 10 to 20 rpm, using spindle #3 or #4 to help ensure that the pointer was within about 20% to about 80% of the dial.

Adhesion Per ASTM D3330/D3330M

Peel adhesion was tested according to ASTM D3330/D3330M-04 "Standard Test Method for Peel Adhesion of Pressure-Sensitive Tape". Adhesion testing was conducted using a 180 degree peel angle and a 12 in/min test speed. For testing purposes, samples were cut into strips having an approximate size of 1" wide by 6" long strips. The release liner was removed and the adhesive side of the sample was applied to a clean test panel. The sample was rolled down twice, each time with a 4.5 pound hand roller, with one roll down occurring once in each lengthwise direction. Thirty minutes of dwell time on the test panel was allowed prior to testing. For tests providing adhesion to steel, the panel was first cleaned with toluene. For tests providing adhesion to polypropylene (PP) or high density polyethylene (HDPE), the panel was first cleaned with isopropyl alcohol. The panels were allowed to dry for 15 minutes after cleaning prior to the sample application. Testing was conducted using an Instron Model 3343 tensile tester, recording the test result as a force per unit of length (in pounds per inch) required to remove the sample from the test panel.

Probe Tack Per ASTM D2979

Probe tack was tested per ASTM D2979-01 "Standard Test Method for Pressure-Sensitive Tack of Adhesives Using Inverted Probe Method". The equipment used to test probe tack included a Probe Tack Tester manufactured by Testing Machines, Inc., which was used with a brass disk and a 5 mm diameter stainless steel probe. The probe was cleaned with a methyl ethyl ketone solvent and dried prior to testing. Probe tack test specimen size was 1 inch by 1 inch.

Shear Test Per PSTC-107

Static shear, often referred to as holding power or hold, was tested on stainless steel panels, with testing conducted according to PSTC-107 Procedure A. For this testing, a contact area of 1 inch by 1 inch was used under a 1 kg load. Shear testing equipment included a ChemInstruments Shear-8 static shear tester with automated control. Time was registered (in minutes) when samples failed, with failure determined by detachment of the sample from the test panel, which resulted in dropping of the attached weight and stopping the built in timer.

Bio-Compatibility Per ISO 10993-5

Bio-compatibility and cytotoxicity testing methodology and results are described with reference to testing of sample C1. The test article was evaluated for potential cytotoxic effects using an in vitro mammalian cell culture test. This study was conducted following the guidelines of ISO 10993-5, Biological evaluation of medical devices—Part 5: Tests for in vitro cytotoxicity. A single preparation of the test article was extracted in single strength Minimum Essential Medium (IX MEM) at 37° C. for 72 hours. The negative control, reagent control, and positive control were similarly prepared. Triplicate monolayers of L-929 mouse fibroblast cells were dosed with each extract and incubated at 37° C. in the presence of 5% $CO_2$ for 48 hours. Following incubation, the monolayers were examined microscopically for abnormal cell morphology and cellular degeneration. The test article extract showed no evidence of causing cell lysis or toxicity. The test article extract met the requirements of the test since the grade was less than or equal to a grade 2 (mild reactivity). The actual sample C1 test grade was 0 (no reactivity).

For skin wear testing, the samples reported in Tables 8 and 9 (on either non-woven cloth or PET film backing, the example substrates used for the associated tests) were cut to a size of about 1 inch by 1.5 inch. Each sample had a protective paper liner that was removed, and the sample was applied with the adhesive side contacting the skin. These samples held on skin for over 18 hours of active wear, including physical exercise, such as about an hour on a treadmill and during a shower. No irritation, redness, or adhesive residue was observed. Samples with the magnetic filler were removed with less pain and were repositioned multiple times without detaching from the skin or showing noticeable edge lift, as compared to corresponding adhesives without a ferromagnetic filler. For example, the rubber based composition that was the subject of composition example G2 (no magnetic filler) lifted from skin and detached after 6 hours of skin wear testing, and rubber based composition G1 (with magnetic filler) held on to skin for over 18 hours of active wear, at which point testing was discontinued, suggesting the composition G1 may have held for even longer than 18 hours. The test findings related to samples G1 and G2 indicate that, in a composition using a rubber based adhesive, adding ferromagnetic filler also resulted in significantly improved skin wear duration without lifting of the adhesive from skin.

Magnetism

Adhesive composition samples containing ferromagnetic filler could be magnetized. For example, the composition used in sample A1 was magnetized as shown by attraction to a neodymium magnet. As discussed more below, samples were able to be magnetized in wet form (e.g., during the coating process) and/or in dry form (e.g., after coating and drying). In conducting the testing of magnetic properties of sample A1, a stack of 20 neodymium magnets was used, each magnet having a diameter of about 1.26 inches and a height of about 0.08 inches. A force was required to separate sample A1 from the stack of magnets. The force required to separate magnetized sample A1 at one inch width from the stack of magnets was approximately 6 mN. The range of the interaction force between the sample and the stack of magnets was registered from 0.2 to 21 mN. Hovering the sample over the stack of magnets resulted in higher force registered by the scale used, about 14 to about 21 mN, compared to pulling it away from the magnet after direct contact (0.2 to 9 mN). The force was measured using a balance scale. The stack of magnets was placed on the weighing pan of the scale and the sample was placed on top of the magnet stack. As the sample was pulled away from the stack of magnets by hand, the net weight registered by the scale decreased. The maximum weight change registered by the scale in grams was converted to Newtons to report the separation force. Two types of balance scales were used with similar test results: a Torbal Precision Scale AD3200 with readability of 0.01 g and a Torbal Analytical Balance AGZN200 with readability of 0.0001 g. There was no weight change detected when sample A1 was pulled off directly from the weighing pan, without a magnet stack. Moreover, it was found that the sample adhesive composition used in sample A1 deviated the arrow of a compass up to about 100 degrees from the resting position, which was pointing north in the resting position.

Magnetic properties of the sample A1 were also evaluated using AC/DC magnetic Meter Model M100 equipped with Hall Effect Sensor with Auto Temperature Compensation manufactured by Extech Instruments. Measurements were taken in b2 screen for 0.1 Gauss DC resolution and Range 1 of 3,000 Gauss maximum. Test data were collected in data recording mode to register maximum and minimum readings. The stack of magnets used in paragraph 41 was measured at 2337 to 2501 Gauss, the sample A1 was tested at 0.3 to 1.0 Gauss. For comparison, a common refrigerator magnet was tested at 860 to 895 Gauss. The magnetic field of the sample A1 is several orders of magnitude lower than commercially available magnets. It is understood that the disclosed magnetic compositions can be magnetized to various degrees of magnetic flux density, for example by varying the process and/or properties of magnets or instruments used to magnetize the compositions. Although relatively weak compared to some magnets, the magnetic adhesives described herein could be used in any of a variety of medical, commercial, personal, and/or industrial applications, or other applications, or any combination thereof where such magnetized materials might be required.

For another example, the adhesive composition used in sample C1 was coated directly on 2 mil PET film by two polished 316L stainless steel rods with chrome finish. It was noticed that the adhesive composition used in sample C1, which includes magnetic filler, was magnetized during this coating process. While the resulting magnetic field in this example was too weak to be measured by a magnetic field meter, the resulting magnetic field could be detected by deviation of a compass arrow. It is understood that the adhesive composition used in sample C1 or other samples may be magnetized before, during, or after coating, for example with other types of stainless steel or other magnetizing materials, and/or the adhesive composition may be magnetized in a dry form (e.g., after coating and drying). For example, some examples are provided below in which the adhesive composition is applied to a nonwoven substrate, such as sample A1, for example. When using a nonwoven substrate, a roller may force the composition through the pores of the substrate, and so other coating methods may be used. Even if not using a magnetizing roller, the adhesive composition may be magnetized before, during, or after coating by any of a variety of magnetizing methods. For example, the adhesive composition with magnetic filler may simply be moved across a magnet or magnetizing instrument in sufficiently close proximity to magnetize the composition, as was done for the sample A1. It was noticed that magnetizing during the coating process by use of stainless steel rods was one convenient way of magnetizing the magnetic filler in the adhesive composition used in preparing sample C1.

EXAMPLES

Further disclosure and description is made with reference to the following examples, which are provided for illustrative purposes only. Exemplary compositions discussed below are presented in Table 1 along with select properties of those compositions.

TABLE 1

Properties and Characteristics of Various Adhesive Compositions

| Sample Name | Adhesive Type | Base Adhesive | Filler | Total Solids (wt %) | Viscosity (cPs) | Solvent blend* | Filler content (wt % wet) | Filler content (wt % dry) | Substrate/Backing |
|---|---|---|---|---|---|---|---|---|---|
| A1 | acrylic | DT129A | HM410 | 59 | 4,500 | EA, | 30 | 51 | non-woven cloth |
| A2 | acrylic | DT129A | No filler | 51 | 3,205 | IPA, H, T | 0 | 0 | non-woven cloth |

TABLE 1-continued

Properties and Characteristics of Various Adhesive Compositions

| Sample Name | Adhesive Type | Base Adhesive | Filler | Total Solids (wt %) | Viscosity (cPs) | Solvent blend* | Filler content (wt % wet) | Filler content (wt % dry) | Substrate/Backing |
|---|---|---|---|---|---|---|---|---|---|
| B1 | acrylic | Aroset 280 | HM410 | 60 | 18,700 | H, EA, T | 30 | 50 | non-woven cloth |
| B2 | acrylic | Aroset 280 | No filler | 53 | 8,660 | | 0 | 0 | non-woven cloth |
| C1 | acrylic | DT129A | HM410 | 59 | 4,500 | EA, | 30 | 51 | 2 mil PET film |
| C2 | acrylic | DT129A | No filler | 51 | 3,205 | IPA, H, T | 0 | 0 | 2 mil PET film |
| D1 | acrylic | Aroset 280 | HM410 | 60 | 18,700 | H, EA, T | 30 | 50 | 2 mil PET film |
| D2 | acrylic | Aroset 280 | No filler | 53 | 8,660 | | 0 | 0 | 2 mil PET film |
| E | acrylic | DT129A | Talc | 59 | 34,560 | EA, | 30 | 51 | non-woven cloth |
| F | acrylic | DT129A | Talc | 59 | 34,560 | IPA, H, T | 30 | 51 | 2 mil PET film |
| G1 | rubber | Morstik 153 | HM410 | 58 | 1,610 | H, T, | 30 | 51 | 2 mil PET film |
| G2 | rubber | Morstik 153 | No filler | 50 | 2,270 | MEK | 0 | 0 | 2 mil PET film |

*Organic Solvents: H = Heptane, T = Toluene, EA = Ethyl Acetate, IPA = Isopropyl Alcohol MEK = Methyl Ethyl Ketone Example 1

The formulation and select properties of a first example adhesive composition are shown in Table 1 as sample A1. In this example, sample A1 was prepared by combining approximately 183 gram of dry filler, which is HM410 strontium ferrite powder, in a glass container with approximately 80 grams of toluene to obtain wet HM410 powder to prevent agglomeration of the filler particles when mixing it with base adhesive. It is understood that other organic solvents may be used to wet the magnetic powder, such as IPA, MEK, Heptane, Ethyl Acetate, Ethyl Alcohol, DMSO or other solvent or any mixture thereof. Any other solvent that is compatible with the base adhesive composition, or solvent blend as listed in Table 1, may be used to mix with the filler. In sample A1 and other samples in Table 1, toluene was merely selected as a convenient solvent to mix with the dry filler to wet the filler. In addition, wetting or compatibility agents may be included if desired to improve dispersibility of magnetic filler in base polymer matrix, for example, a siloxane type agent. The wet HM-410 powder was transferred into a glass container with 351 gram of Henkel DURO-TAK 129A adhesive and mixed using a lab mixer for about 10 minutes to achieve an approximately homogeneous adhesive/powder mix or composition. The viscosity of the A1 adhesive is presented in Table 6 as tested initially and after storing adhesive at room temperature for 3 weeks. There was no detectable viscosity build up, and the adhesive was usable after storage as its coatability did not change.

A draw-down sample was prepared by applying a coating of the sample A1 composition mix at a thickness of approximately 2 mils onto a paper release liner (Loparex Grade 52564 at 2 mil thickness), resulting in a linered sample having an adhesive side and a liner side. The linered sample was dried for about 5 minutes at room temperature, and then for an additional 5 minutes in an oven at 107° C. to allow the solvent (toluene) to evaporate. The linered sample was laminated at room temperature to a non-woven polyester cloth substrate (Sontara Style 8010 with basis weight of about 1.34 ounces per square yard), with the adhesive side of the sample facing or contacting the cloth substrate. Following the room temperature lamination of the sample to the cloth substrate, the laminate was further laminated using a hot roll laminator set at 66° C., resulting in tape sample A1. Tape sample A1 was conditioned for about 24 hours at room temperature prior to testing.

Calculations used to determine various weight percentages of sample A1 are shown in Table 2, along with similar calculations for sample C1, which is essentially the same adhesive composition applied to a different substrate than A1. Sample C1 is described in more detail in Example 5.

TABLE 2

Weights and Percentages of Composition Samples A1 and C1

| Sample Name | Component | | Actual wet weight (g) | % solids | Actual dry weight (g) | wt. % |
|---|---|---|---|---|---|---|
| A1 and C1 | DT129 | Base adhesive, solvent acrylic PSA | 351 | 51 | 179 | 49 |
| | HM 410 | Ferromagnetic filler, Strontium Ferrite | 183 | 100 | 183 | 51 |
| | Solvent | Toluene | 80 | 0 | 0 | 0 |
| | | Total: | 614 | | 362 | 100 |
| | | | | | % wet wt solids | 59 |
| | | | | | % dry wt filler | 51 |
| | | | | | % wet filler | 30 |

Example 2

The formulation and select properties of a second example adhesive composition are shown in Table 1 as sample A2. Sample A2 is provided for comparative purposes as it uses the same base adhesive as sample A1, but the magnetic filler HM410 with extra toluene to wet HM410 powder was not included in the preparation of sample A2. A draw-down sample was prepared by applying a coating of Henkel DURO-TAK 129A base adhesive at a thickness of approximately 2 mils onto a paper release liner (Loparex Grade 52564 at 2 mil thickness), resulting in a linered sample having an adhesive side and a liner side. The linered sample was dried for about 5 minutes at room temperature, and then for an additional 5 minutes in an oven at 107° C. to allow the solvent (toluene) to evaporate. The linered sample was laminated at room temperature to a non-woven polyester cloth substrate (Sontara Style 8010 with basis weight of about 1.34 ounces per square yard), with the adhesive side of the lined sample facing or contacting the cloth substrate. Following the room temperature lamination of the sample to the cloth substrate, the laminate was further laminated using a hot roll laminator set at 66° C., resulting in tape sample A2. Tape sample A2 was conditioned for about 24 hours at room temperature prior to testing.

Example 3

The formulation and select properties of a third example adhesive composition are shown in Table 1 as sample B1. Sample B1 is similar to sample A1, except that the base adhesive used in sample B1 is Ashland AROSET 280 instead of Henkel DURO-TAK DT129A. In this example, sample B1 was prepared by combining approximately 143 grams of dry HM410 strontium ferrite powder in a glass container with approximately 61 grams of toluene resulting in a wet powder. The wet powder was transferred into a glass container with 274 grams of Ashland AROSET 280 base adhesive and mixed using a lab mixer for about 10 minutes to achieve an approximately homogeneous adhesive/powder mix or composition. The viscosity of the B1 adhesive is presented on Table 7 as tested initially and after 2 days at room temperature. There was a noticeable viscosity increase after 2 days of adhesive storage. It is understood that such an increase in viscosity may result in an adhesive based on sample B1 that could be relatively difficult to coat after 2 days. A draw-down sample was prepared by applying a coating of the composition mix at a thickness of approximately 2 mils onto a paper release liner (Loparex Grade 52564 at 2 mil thickness), resulting in a linered sample having an adhesive side and a liner side. The linered sample was dried for about 5 minutes at room temperature, and then for an additional 5 minutes in an oven at 107° C. to allow the solvent to evaporate. The linered sample was laminated at room temperature to a non-woven polyester cloth substrate (Sontara Style 8010 with basis weight of about 1.34 ounces per square yard), with the adhesive side of the linered sample facing or contacting the cloth substrate. Following the room temperature lamination of the linered sample to the cloth substrate, the laminate was further laminated using a hot roll laminator set at 66° C., resulting in tape sample B1. Tape sample B1 was conditioned for about 24 hours at room temperature prior to testing.

Calculations used to determine various weight percentages of sample B1 are shown in Table 3, along with similar calculations for sample D1 described in more detail in Example 7.

TABLE 3

Weights and Percentages of Composition Samples B1 and D1

| Sample Name | Component | | Actual wet weight (g) | % solids | Actual dry weight (g) | wt. % |
|---|---|---|---|---|---|---|
| B1 and D1 | Aroset 280 | Base adhesive, solvent acrylic PSA | 274 | 53 | 145 | 50 |
| | HM 410 | Ferromagnetic filler, Strontium Ferrite | 143 | 100 | 143 | 50 |
| | Solvent | Toluene | 61 | 0 | 0 | 0 |
| | | Total: | 478 | | 288 | 100 |
| | | | | | % solids | 60 |
| | | | | | % dry filler | 50 |
| | | | | | % wet filler | 30 |

Example 4

The formulation and select properties of a fourth example adhesive composition are shown in Table 1 as sample B2. Sample B2 is provided for comparative purposes as it is substantially similar to sample B1, except magnetic filler was not included in the preparation of sample A2. Sample B2 is also similar to sample A2, in that both were prepared without adding magnetic filler, but differ in that sample B2 was prepared using base adhesive AROSET 280 instead of base adhesive DURO-TAK 129A used in sample A2. In example 4, a draw-down sample was prepared by applying a coating of Ashland AROSET 280 base adhesive at a thickness of approximately 2 mils onto a paper release liner (Loparex Grade 52564 at 2 mil thickness), resulting in a linered sample having an adhesive side and a liner side. The linered sample was dried for about 5 minutes at room temperature, and then for an additional 5 minutes in an oven at 107° C. to allow the solvent (toluene) to evaporate. The linered sample was laminated at room temperature to a non-woven polyester cloth substrate (Sontara Style 8010 with basis weight of about 1.34 ounces per square yard), with the adhesive side of the linered sample facing or contacting the cloth substrate. Following the room temperature lamination of the lined sample to the cloth substrate, the laminate was further laminated using a hot roll laminator set at 66° C., resulting in tape sample B2. Tape sample B2 was conditioned for about 24 hours at room temperature prior to testing

Examples 5 Through 8

Examples 5-8 were prepared in similar manner to examples 1-4, except that in examples 5-8 the adhesive compositions were directly coated onto 2 mil PET film rather than coated to a paper liner and then transfer laminated to a non-woven polyester cloth, and a different liner was used and applied differently. Samples A1 and C1 used essentially the same adhesive composition, applied to the different respective substrates to provide respective examples 1 and 5. Samples A2 and C2 used the same adhesive composition, applied to the different respective substrates to provide respective examples 2 and 6. Samples B1 and D1 used the same adhesive composition, applied to the different respective substrates to provide respective examples 3 and 7. Samples B2 and D2 used the same adhesive composition, applied to the different respective substrates to provide respective examples 4 and 8.

For example, the formulation and select properties of a third example adhesive composition are shown in Table 1 as sample C1. In this example, sample C1 was prepared by combining approximately 183 gram of dry filler, which is HM410 strontium ferrite powder, in a glass container with approximately 80 grams of toluene to obtain wet HM410 powder to prevent agglomeration of the filler particles when mixing it with base adhesive. The wet HM-410 powder was transferred into a glass container with 351 gram of Henkel DURO-TAK 129A adhesive and mixed using a lab mixer for about 10 minutes to achieve an approximately homogeneous adhesive/powder mix or composition. The viscosity of the C1 adhesive is presented in Table 10. A draw-down sample C1 was prepared by applying a coating of the composition mix at a thickness of approximately 2 mils onto a 2 mil PET film substrate and covered with a paper release liner.

In examples 5-8 (samples C1-D2) using 2 mil PET film substrate, the liner used was Loparex S42# SB SCK Grade 54154 instead of Loparex Grade 52564 as used in examples 1-4. The liner was also applied differently, as discussed above. In examples 5-8, adhesive composition with magnetic filler was coated on the PET film substrate. The coated sample was dried for 5 minutes at room temperature then for an additional 5 minutes in an oven at 107° C. to allow the solvent to evaporate. The adhesive side of the coated sample was then covered with the protective paper release liner Loparex 542# SB SCK Grade 54154. The linered samples were then conditioned at 24 hours at room temperature prior to testing, as were the samples in examples 1-4.

Other than the change in substrate or backing and liner, the composition and preparation of example 5 corresponds to that described above in example 1 (DT129A base adhesive with magnetic filler), the composition and preparation of example 6 corresponds to that described above in example 2 (DT129A base adhesive without magnetic filler), the composition and preparation of example 7 corresponds to that described above in example 3 (AROSET 280 base adhesive with magnetic filler), and the composition and preparation of example 8 corresponds to that described above in example 4 (AROSET 280 base adhesive without magnetic filler). In examples 5-8, the 2 mil PET film used was Transcendia TransPET GPHH-F 200 gauge, which was used instead of the non-woven polyester cloth Sontara Style 8010 used in examples 1-4 as discussed above.

Calculations used to determine various weight percentages of samples C1 and D1, are shown above in Tables 2 and 3, respectively.

Examples 9 and 10

The formulation and select properties of the adhesive compositions of examples 9 and 10 are shown in Table 1 as samples E and F, respectively. Samples E and F are provided for comparative purposes as the adhesive compositions are substantially similar to sample A1, except magnetic filler was not included but rather replaced with an approximately equal amount talc filler in the preparation of samples E and F. The talc used in examples 9 and 10 was Grade 400-LB, commercially available from Natural Minerals. The resulting adhesive composition in sample E was applied to Sontara Style 8010 non-woven polyester cloth, whereas the resulting adhesive composition in sample F was applied to Transcendia TransPET GPHH-F 200 gauge 2 mil PET film. For sample E in example 9, the composition and draw-down procedures or preparations were similar to those described in example 1 as applied to sample A1. For sample F in example 10, the composition mixing and preparation procedures were similar to those described in example 1 as applied to sample A1, while the draw-down procedures or preparations were similar to those described in example 5 as applied to sample C1.

Calculations used to determine various weight percentages of samples E and F are shown in Table 4.

TABLE 4

Weights and Percentages of Composition Samples E and F

| Sample Name | Component | | Actual wet weight (g) | % solids | Actual dry weight (g) | wt. % |
|---|---|---|---|---|---|---|
| E and F | DT129A | Base adhesive, solvent acrylic PSA | 351 | 51 | 179.01 | 49 |
| | Talc | Non-ferromagnetic filler | 183 | 100 | 183 | 51 |
| | Solvent | Toluene | 80 | 0 | 0 | 0 |
| | | Total: | 614 | | 362.01 | 100 |
| | | | | | % solids | 59 |
| | | | | | % dry filler | 51 |
| | | | | | % wet filler | 30 |

Example 11

The formulation and select properties of an eleventh example adhesive composition are shown in Table 1 as sample G1. Example 11 with sample G1 are provided, for example, as an alternative embodiment to example 5 and sample C1 and for comparative purposes thereto, each of which describes an adhesive composition applied to 2 mil PET film (TransPET GPHH-F). In example 11, sample G1 is prepared using a rubber based solvent adhesive Morstik 153 from Dow Adhesives (The Dow Chemical Company) instead of the acrylic based solvent adhesive DURO-TAK 129A described and used in example 5 and/or sample C1, except the sample was dried in the oven at a different temperature (89° C. instead of 107° C.).

In example 11, sample G1 was prepared by combining approximately 183 grams of dry HM410 strontium ferrite powder in a glass container with approximately 80 grams of toluene resulting in a wet powder. The wet powder was transferred into a glass container with 351 grams of Morstik 153 rubber base adhesive and mixed using a lab mixer for about 10 minutes to achieve an approximately homogeneous adhesive/powder mix or composition.

In example 11, the resulting adhesive composition with magnetic filler was applied directly to the 2 mil PET film substrate TransPET GPHH-F 200 gauge to provide a draw-down sample. The coated sample was dried for 5 minutes at room temperature then for an additional 5 minutes in an oven at 89° C. to allow the solvent to evaporate. The adhesive side of the coated sample was then covered with the protective paper release liner Loparex S42# SB SCK Grade 54154. The linered samples were then conditioned at 24 hours at room temperature prior to testing.

Calculations used to determine various weight percentages of sample G1 are shown in Table 5.

TABLE 5

Weights and Percentages of Composition Sample G1

| Sample Name | Component | | Actual wet weight (g) | % solids | Actual dry weight (g) | wt. % |
|---|---|---|---|---|---|---|
| G1 | Morstik 153 | Base adhesive, solvent acrylic PSA | 270 | 50 | 135 | 49 |
| | HM 410 | Ferromagnetic filler, Strontium Ferrite | 138 | 100 | 138 | 51 |
| | Solvent | Toluene | 60 | 0 | 0 | 0 |
| | | Total: | 468 | | 273 | 100 |
| | | | | | % solids | 58 |
| | | | | | % dry filler | 51 |
| | | | | | % wet filler | 30 |

Example 12

The formulation and select properties of a twelfth example adhesive composition are shown in Table 1 as sample G2. Sample G2 is provided for comparative purposes as it is substantially similar to sample G1, except magnetic filler was not included in the preparation of sample G2. A draw-down sample was prepared by applying the resulting composition (without magnetic filler) directly to the 2 mil PET film substrate TransPET GPHH-F 200 gauge. The coated sample was dried for 5 minutes at room temperature then for an additional 5 minutes in an oven at 89° C. to allow the solvent to evaporate. The adhesive side of the coated sample was then covered with the protective paper release liner Loparex 542# SB SCK Grade 54154.

Examples 13 Through 17

Comparison examples 13 through 17, based on adhesive compositions C1 and C3 through C7, are shown in Table 10, discussed in more detail below. Composition C3 is a diluted form of composition C2 and is the subject of example 13. C3 was prepared in the same way as C2, with essentially no magnetic filler, but was diluted to 41% solids by weight. Compositions C4 and C5 form examples 14 and 15, respectively, and were prepared in much the same way as composition C1, but with varying amounts of magnetic filler, 5% and 25%, respectively. Composition C1 is included again in Table 10 for reference, having a filler content of 51%. Compositions C6 and C7 form examples 16 and 17, respectively, and were prepared in much the same was as composition C1, but with varying amounts of magnetic filler, 75% and 95%, respectively. Table 10 shows that with increasing filler content the composition's viscosity increases. Table 10 also illustrates the wide range of magnetic filler (about 5% to 95%) that may be used. Depending on the magnetic filler content and/or magnetization, the resulting compositions may exhibit pressure sensitive properties (e.g., samples C3, C4 and C5) or may not display such properties (e.g., samples C1, C6 and C7).

Tables 6 through 9 show various properties of various compositions. Table 6 shows the viscosity of composition sample A1 described in more detail above in Example 1. The viscosity of sample A1 was tested immediately after mixing and after 3 weeks at room temperature (R.T.). Table 7 shows the viscosity of composition sample B1 tested immediately after mixing and after 2 days at R.T. Coating of an adhesive composition may be facilitated by maintaining the composition at a low viscosity or within a certain viscosity range. For example, a target range for viscosity of a wet adhesive composition may be between about 1500 and about 9000 cPs, although it is understood that compositions outside of this range may still be workable for coating a substrate or surface. Tables 6 and 7 show that sample A1 has a lower viscosity than sample B1, and for that reason may be for suitable or easier to use as an adhesive for coating purposes.

TABLE 6

Viscosity at Time Intervals of Composition Sample A1
Sample A1 Adhesive Viscosity

| Time after mixing | Tested Immediately after mixing | Retest after 3 weeks at R.T. |
|---|---|---|
| Brookfield Viscosity, cPs 20 rpm, # 4 spindle at R.T. | 4,500 | 4,340 |

TABLE 7

Viscosity at Time Intervals of Composition Sample B1
Sample B1 Adhesive Viscosity

| Time after mixing | Tested Immediately after mixing | Retest after 2 days at R.T. |
|---|---|---|
| Brookfield Viscosity, cPs 10 rpm, # 4 spindle at R.T. | 18,700 | 61,670 |

Table 8 shows various adhesive properties of various samples applied to non-woven cloth as described above (samples A1, A2, E, B1, and B2). Table 9 shows various adhesive properties of various samples applied to 2 mil PET film as described above (samples C1, C2, F, D1, D2, G1, and G2). Several of the samples listed in Tables 8 and 9 displayed relatively low adhesion and/or probe tack values. For example, samples, C1, D1, and G1, when tested, showed essentially no adhesion to steel, to polypropylene, or to high density polyethylene. These samples also were tested to have essentially no probe tack. These findings were unexpected since the samples were in fact quite effective at maintaining hold to human skin. As discussed above under the section discussing bio-compatibility per ISO 10993-5, skin wear testing showed these samples held to skin for over 18 hours of activity, including physical exercise and showering. Samples with approximately zero lb/in adhesion to steel, PP, and HDPE, such as samples C1, D1, and G1, that also had approximately zero minutes static shear or hold at 70 degrees C. and zero gram probe tack were able to hold or have static shear properties to skin for about one minute or more, for about 5 minutes or more, for about 1 hour or more, for about 6 hours or more, for about 12 hours or more, and/or for about 18 hours or more.

TABLE 8

Adhesive Properties of Various Samples Applied to Non-Woven Cloth

| Property | A1 HM410 in DT129A | A2 DT129A | E talc in DT129A | B1 HM410 in Aroset 280 | B2 Aroset 280 |
|---|---|---|---|---|---|
| Adhesion to steel, lb/in | 3.8 | 3.9 | 1.5 | 2.0 | 7.8 |
| Adhesion to PP, lb/in | 1.0 | 1.7 | 0.8 | 0.5 | 1.3 |
| Adhesion to HDPE, lb/in | 0.5 | 0.9 | 0.5 | 0.2 | 0.6 |
| Probe tack, g | 234 | 289 | 62 | 158 | 370 |
| Hold at 70° C., min | 50 | 23 | 2 | 7 | 9 |

TABLE 9

Adhesive Properties of Various Samples Applied to 2 mil PET Film

| Property | C1 HM410 in DT129A | C2 DT129A | F talc in DT129A | D1 HM410 in Aroset 280 | D2 Aroset 280 | G1 HM410 in Morstik 153 | G2 Morstik 153 |
|---|---|---|---|---|---|---|---|
| Adhesion to steel, lb/in | 0.1 | 3.9 | 1.2 | 0.0 | 4.9 | 0.0 | 10.2 |
| Adhesion to PP, lb/in | 0.0 | 2.3 | 0.55 | 0.0 | 2.5 | 0.0 | 6.9 |
| Adhesion to HDPE, lb/in | 0.0 | 1.0 | 0.1 | 0.0 | 0.7 | 0.0 | 4.3 |
| Probe tack, g | 0 | 1419 | 247 | 0 | 1448 | 0 | 1629 |
| Hold at 70° C., min | 0 | 66 | 162 | 0 | 449 | 0 | 33 |

Tables 8 and 9 also show that adhesive compositions using talc as a filler, rather than HM410, did not display the magnetic properties associated with HM410, and did not result in the unique and unexpected property of having essentially zero adhesion and probe tack. The test results shown in Tables 8 and 9 indicate that the only samples prepared, as discussed above, that show the property of zero adhesion and probe tack while maintaining hold to skin are those that include magnetic filler that has been magnetized. In the cases of samples C1, D1, and G1, shown in Table 9 and discussed in more detail above, the magnetic filler HM410 was magnetized by the coating process including steel rollers.

Table 10 shows various properties, including viscosity and adhesion of various compositions with variable filler content. In general, the sample compositions shown in Table 10 are based on samples C1 and C2 described above and shown in Table 1, with the various samples C3-C7 provided by varying the filler content. As described above, sample C1 includes 51 dry wt. % HM410 filler. Sample C3 was provided by diluting sample C2, which has no HM410 filler content. For testing purposes, it was necessary to add extra solvent (80 g toluene, total) to wet the powder of sample C7 because the content of HM410 powder was so high. In order to keep the amount of solvent consistent across the samples, 80 grams of toluene was used in all samples reported in Table 10. Sample C2 did not have as much toluene as sample C7, so it was diluted by adding extra toluene to arrive at the same amount of total toluene as sample C7. Samples C1 and C4-C7 were provided by varying the HM410 filler content between 5 dry wt. % and 95 dry wt. %, as shown in Table 10. As can be seen in Table 10, samples C1, C6, and C7, which have 51% or more HM410 filler content (dry wt. %), each displayed the unique and unexpected property of measuring essentially no adhesion or probe tack, yet bonded to skin for over 18 hours of activity, including physical exercise and showering.

It is noted that comparing properties associated with the adhesive composition used in samples A1 and C1 vary depending on whether non-magnetized (sample A1) or magnetized (sample C1). The unique and unexpected property of displaying essentially no adhesion or tack while still holding to skin for 18 hours of activity is present in sample C1 which was magnetized by the steel roller. Sample A1, though holding to skin for 18 hours or more, does display adhesion and tack as indicated in Table 8. Sample A1, based on the same adhesive composition, was not magnetized by a roller.

TABLE 10

Properties Based on Samples C1 and C2 and Variations

| Sample Name | HM410 Filler Content (dry wt. %) | Solids (wt. %) | Viscosity (cPs) | Adhesion to steel (lb/in) | Adhesion to PP (lb/in) | Probe Tack (g) |
|---|---|---|---|---|---|---|
| C3 | 0 | 41 | 1,395 | 5.5 | 3.1 | 1745 |
| C4 | 5 | 45 | 1,711 | 5 | 3.2 | 1617 |
| C5 | 25 | 50 | 2,150 | 3.5 | 2.3 | 1049 |
| C1 | 51 | 66 | 4,190 | 0 | 0 | 0 |
| C6 | 75 | 64 | 8,750 | 0 | 0 | 0 |
| C7 | 95 | 75 | 85,600 | 0 | 0 | 0 |

FIG. 1 illustrates in a graph the relationship between the viscosity of the adhesive compositions C3 through C7 (y-axis) and percent solids (x-axis), as listed in the Table 10. FIG. 1 shows that, with an increase in percent solids corresponding to the increase in filler content, the resulting compositions each had a viscosity in a range suitable to be processed by conventional adhesive coating methods. The trend line representing the viscosity as a function of percent solids may be expressed by the equation $y=1369.6e^{0.0235x}$ as shown for example in FIG. 1.

These illustrative compositions, having the indicated viscosities in this range, may be suitable for use in some embodiments of a magnetic medical or transdermal adhesive composition.

Modifications and variations may be practiced by those of ordinary skill in the art without departing from the spirit and scope, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the scope of that which is described in the claims. Therefore, the spirit and scope of the appended claims should not be limited to the exemplary description of the versions contained herein.

I claim:

1. An adhesive composition, comprising: (1) 5-50% of a polymer matrix base pressure sensitive adhesive suitable for use on skin and (2) 50-95% of ferromagnetic filler, wherein the ferromagnetic filler is magnetized such that the adhesive composition measures about 0 lb/in adhesion to steel and/or polypropylene as tested according to the ASTM D3330/D3330M-04 "Standard Test Method for Peel Adhesion of Pressure-Sensitive Tape", about 0 minutes static shear as tested according to PSTC-107 Procedure A, and about 0 gram probe tack as tested according to ASTM D2979-01 "Standard Test Method for Pressure-Sensitive Tack of Adhesives Using Inverted Probe Method", and wherein the adhesive composition passed ISO 10993-5 bio-compatibility test.

2. The adhesive composition of claim 1, wherein the polymer matrix is polyacrylate, rubber based, polyurethane, epoxy, or silicone, or a mixture thereof.

3. The adhesive composition of claim 1, wherein the adhesive composition is capable of passing the ISO 10993-5 elution toxicity test with a score of 0 or 1 as provided in the third edition (2009 Jun. 6).

4. The adhesive composition of claim 1, wherein the magnetic filler is strontium ferrite.

5. The adhesive composition of claim 4, wherein the magnetic filler is strontium ferrite in powdered form.

6. The adhesive composition of claim 5, wherein the powdered strontium ferrite is a powder with average particle size between about 1.65 microns to about 4.6 microns.

7. The adhesive composition of claim 1, wherein the adhesive composition is effective on skin when applied to a substrate with a thickness in the range of about 0.3 mils to about 7 mils.

8. The adhesive composition of claim 1, wherein the magnetic filler is present in a dry weight percentage in the range of about 50% to about 95%.

9. A tape including a bio-compatible magnetic adhesive, comprising:
the adhesive composition of claim 1; and
a substrate suitable for lamination with the adhesive composition; wherein the adhesive composition is laminated to the substrate to form a bio-compatible magnetic adhesive tape.

10. The tape of claim 9, further comprising a paper liner.

11. The tape of claim 9, wherein the substrate is at least one of nonwoven cloth and PET film.

12. The tape of claim 9, wherein the bio-compatible adhesive composition is capable of passing the ISO 10993-5 elution toxicity test with a score of 0 or 1 as provided in the third edition (2009 Jun. 1).

13. The tape of claim 9, wherein the polymer matrix base pressure sensitive adhesive comprises polyacrylate, rubber based, polyurethane, epoxy, or silicone, or a mixture thereof.

14. The tape of claim 9, wherein the magnetized ferromagnetic filler is strontium ferrite.

15. The tape of claim 14, wherein the magnetized ferromagnetic filler is strontium ferrite in powdered form.

16. The tape of claim 15, wherein the powdered strontium ferrite is a powder with average particle size between about 1.65 microns to about 4.6 microns.

\* \* \* \* \*